United States Patent [19]

Nishikawa et al.

[11] Patent Number: 5,128,334
[45] Date of Patent: Jul. 7, 1992

[54] ANALGESIC AND ANTI-INFLAMMATORY MEDICINE

[75] Inventors: Yoshiyuki Nishikawa, Kyoto; Tetsuo Nakamura, Tokyo, both of Japan

[73] Assignee: Immuno Japan Inc., Tokyo, Japan

[21] Appl. No.: 631,974

[22] Filed: Dec. 21, 1990

[30] Foreign Application Priority Data

Dec. 26, 1989 [JP] Japan .................. 1-335087

[51] Int. Cl.$^5$ .................. A61K 31/60; A61K 31/62
[52] U.S. Cl. .................. 514/159; 514/161
[58] Field of Search .................. 514/159, 161

[56] References Cited

PUBLICATIONS

Chem. Abst. vol. 97 (1982) 192744t.
Unlisted Drugs, vol. 17, No. 1., Jan. 1965, p. 4f.
Unlisted Drugs, vol. 26, No. 3., Mar. 1974, p. 41e.
Unlisted Drugs, vol. 21, No. 1., Jan. 1969, p. 10g.
Unlisted Drugs, vol. 21, No. 4., Apr. 1969, p. 55j.
Unlisted Drugs, vol. 20, No. 2., Feb. 1968, p. 20e.
Basu, T. K., "Vitamin C-Aspirin Interactions", *International Journal for Vitamin and Nutrition Research, Supplement* (1982), vol. 23, pp. 83-90.

*Primary Examiner*—S. J. Freidman
*Attorney, Agent, or Firm*—Beveridge, DeGrandi & Weilacher

[57] ABSTRACT

A composition containing ascorbic acid and/or its derivatives and aspirin and/or its derivatives is an effective analgesic and anti-inflammatory medicine. A method for reducing the side effects of aspirin in a mammal involves the administration of an effective amount of a pharmaceutical composition comprising ascorbic acid and/or its derivatives and aspirin/or its derivatives.

15 Claims, 1 Drawing Sheet

ANALGESIC AND ANTI-INFLAMMATORY MEDICINE

INTRODUCTION TO THE INVENTION

The present invention relates to analgesic and anti-inflammatory medicine. Of particular interest is a composition containing ascorbic acid and/or its derivatives and aspirin and/or its derivatives. The present invention also relates to a method for reducing the side effects of aspirin in a mammal, including human beings.

Aspirin, or acetyl salicylic acid, and its derivatives, e.g., aspirin aluminum, or aluminum acetyl salicylate, cholin salicylate, and sodium salicylate, are widely utilized as non-pyrazolone analgesics and non-steroidal anti-inflammatory medicines. Aspirin and its derivatives are known to have more or less therapeutic effects on various diseases, such as rheumatism, hyperuricemia, and hypercoagulopathies due to elevated platelet agglutination, mainly through the mechanism whereby aspirin suppresses biosynthesis of prostagrandins. However, this same mechanism is the principal cause of injury to gastric mucosa. This unfavorable side effect of aspirin is an inevitable problem of its practical use.

Several causes of the injury to gastric mucosa by aspirin have been noted and studied: (1) aspirin causes a structural change of mucous glycoprotein which makes it easily digested by pepsin, (2) aspirin inhibits sulfation of mucous glycoprotein which makes it easily digested by pepsin, (3) aspirin inhibits biosynthesis of prostagrandins followed by inhibition of mucous glycoprotein secretion and promotion of gastric juice secretion, (4) inhibition of oxidative phosphorylation by aspirin stops energy supply, and (5) aspirin directly injures the gastric wall and causes bleeding from it. In short, aspirin adversely affects mucous glycoprotein, prostaglandin, and the gastric wall, and causes serious injury to capillary vessels beneath the mucosa, bleeding from the gastric wall and necrosis of the gastric wall. Bleeding from the stomach leads to ill feeling, loss of appetite, vomiting, and anemia. Precautions should be taken against stomach ulcers, especially when aspirin is given for a long period of time (e.g., treatment of rheumatism in a patient).

One of the methods to avoid the side effects of aspirin is to give aspirin immediately after a meal to reduce the injury caused by gastric juice. But this method may also reduce the efficacy and the immediate effect of aspirin itself, and is not thought to be a fundamental means for the solution of the side effects problem.

A number of people today have stomach ulcers, or its symptoms, caused by stress from various factors. When those people take aspirin constantly, serious injury to gastric mucosa could occur by multiple causes.

Up to the present, buffered aspirins such as Bufferin (trademark of Bristol-Myers Co., U.S.A.) contain an acid-regulator (the constituent for neutralization), which reduce the stimulation of gastric juice. However, insoluble particles of aspirin remain as persistent stomach stimulants.

Other methods to avoid injury and to protect gastric mucous cells have been studied. For example, Daniel Holland, et al. showed a method to protect the stomach from adverse side effects of aspirin by combining arachidonic acid or linoleic acid Japanese patent publication number 62522/84). And Denis Marlon Baily, et al. showed that the cell protective effects of sodium thiosulfate and 3,3'-thiobis-(propanoic acid) could protect gastric mucosa from aspirin.

Ascorbic acid, a constituent of the present invention, is well known as vitamin C, and its role is clear in the biosynthesis of collagen, the biosynthesis of adrenocortical hormone and the inhibition of melanin biosynthesis. The drawback of ascorbic acid is that it attacks vessel endodermis cells, and is followed by severe bleeding such as scurvy.

One of the in vivo studies on the quantitative change in vitamin C caused by taking aspirin in rheumatism patients was made by Sahud, et al. (1971). They reported that the quantity of vitamin C in platelets was reduced by half in the group of patients who had taken large amounts of aspirin compared with those who had taken small amounts or none of it. Another study was made by Russell, et al. (1988). They reported that bleeding from gastric mucosa was increased in a group of guinea pigs that had been given vitamin C deficient feed, compared with the group given normal feed. However, no one has tried to prevent stomach ulcers, caused by taking drugs such as aspirin and its derivatives, by means of positive administration of vitamin C.

SUMMARY OF THE INVENTION

One of the objects of the present invention is to develop an analgesic and anti-inflammatory medicine that solves the injury to gastric mucosa, or the side effects caused by taking aspirin and its derivatives.

According to the present invention, this and other objects are achieved by developing an analgesic and anti-inflammatory medicine containing ascorbic acid and/or one or more of its derivatives, and aspirin and/or one or more of its derivatives.

Another object of the present invention is a method for reducing the side effects of aspirin in a mammal, including humans.

DETAILED DESCRIPTION OF THE INVENTION

Figure 1:
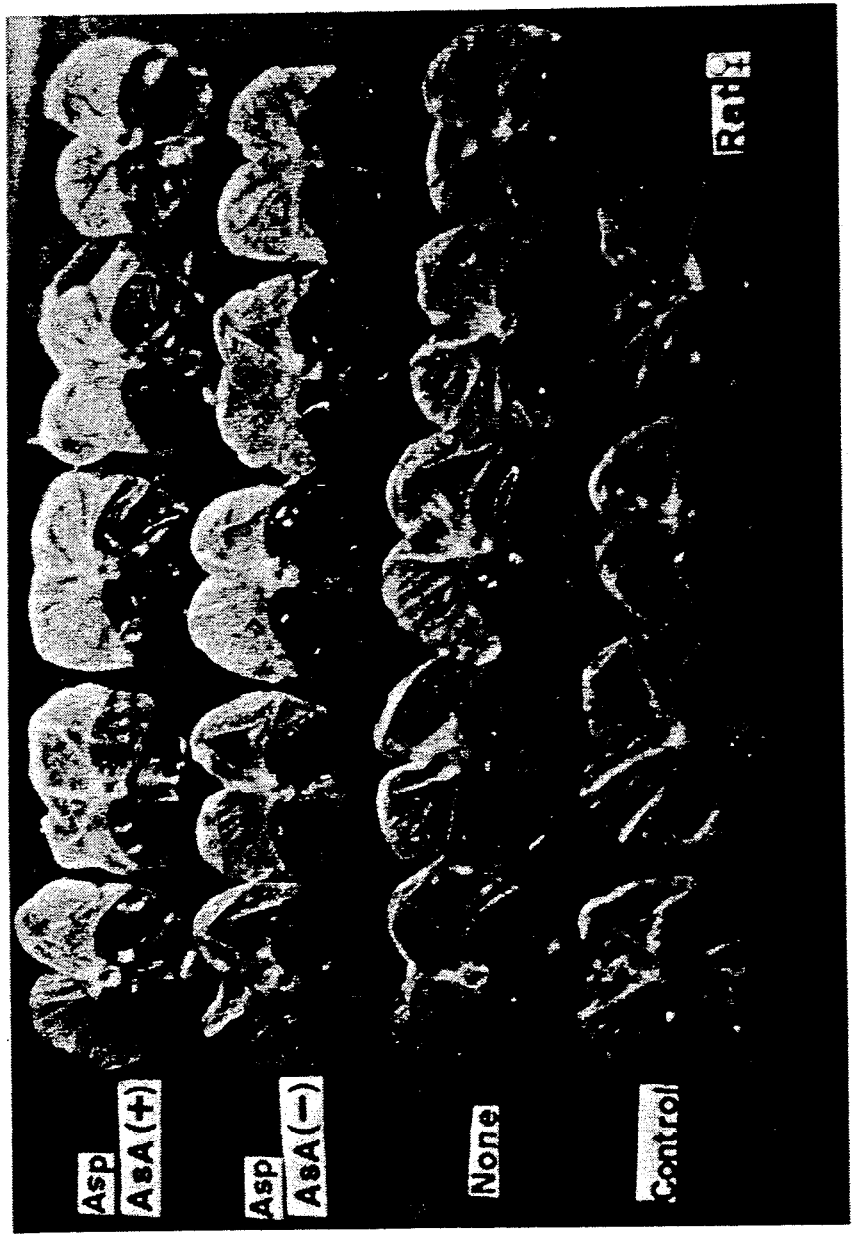
FIG. 1 is a photograph of the insides of the stomach of rats in Example 2. The stomachs were removed after the end of the test. From the top, the first line shows the stomachs of the test group, the second line shows those of the control group A, the third line shows those of the control group B, the fourth line shows those of the control group C. A black area in a stomach shows the outbreak of ulcer.

By taking the medicine of this invention, mammals (including human beings) can efficiently prevent injury to their gastric mucosa which is the characteristic adverse side effect of aspirin and its derivatives, while its analgesic and anti-inflammatory effects are not reduced at all. This was confirmed by standard assay using arthritic rats.

Moreover, the medicine of this invention will not worsen injury to the stomach, but instead will improve it when the mammal (including human beings) that has already suffered from injury to the stomach (such as bleeding or ulcer) takes the medicine.

The derivatives of ascorbic acid that can be utilized in this invention are as follows: Inorganic salts of ascorbic acid, e.g. sodium ascorbate, ascorbic acid esters, e.g. mono stearyl ascorbate, and ascorbic acid esters with inorganic acids, e.g., phosphoric ascorbate.

The derivatives of aspirin that can be utilized in this invention are, for example, aluminum acetylsalicylate, cholin salicylate, sodium salicylate and others.

The medicine of this invention essentially includes ascorbic acid and/or one or more of its derivatives, and aspirin and/or one or more of its derivatives, as described above, and may include other ingredients, for example but not limited to bulking agents or other additives, e.g. silica or starch, or medicine such as acetaminophen. In brief, the medicine which includes the essential ingredients as described above must be contained in this invention.

The medicine provided in this invention is not restricted by the ratio between aspirin derivatives and ascorbic acid derivatives. However, when the medicine includes more than one portion of ascorbic acid derivatives: ten portions of aspirin derivatives by weight, it will have a large preventive effect against injury to gastric mucosa.

The medicine provided in this invention, which contributes to the prevention of the adverse side effect of aspirin, may be in any form (e.g. capsules, tablets, granules, liquid, powder) when administered to mammals (including human beings). One of the favorable forms of the medicine is a gelatin capsule which contains granules of the mixture of aspirin and ascorbic acid, or the mixture added with starch as bulking agent.

The pharmaceutical compositions of this invention may contain the active compounds together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, magnesium carbonate magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compounds together with suitable amount of carrier so as to provide the form for proper administration to the host. While intravenous injection is a very effective form of administration, other modes can be employed.

When the medicine provided in this invention is prescribed to mammals (including human beings), it efficiently prevents characteristic adverse side effects of aspirin and its derivatives, i.e. injury to gastric mucosa, while it completely retains the analgesic and anti-inflammatory effects of aspirin and its derivatives.

This medicine is also useful in mammals (including human beings) that already have stomach injury, i.e. bleeding or ulcer, caused by stress. It will not make the condition worse, instead it will improve it.

The following are examples of the medicine provided in this invention. But they are not intended to restrict or limit the field of this invention.

The tests for side effects which were made on mice and rats may, as a matter of course, represent the effect in mammals (including human beings), although diagnostic tests have not been made.

EXAMPLES

Example 1

Demonstration of the effect in mice —Effect of the medicine provided in this invention against ulcers concurrently caused by administration of aspirin and the stress caused by immersion in water Mice were exposed to stress by being soaked in water after administration of the medicine provided in this invention. Male and female I.C.R. mice (16 to 17 weeks of age, primarily weighing 32 to 58 grams) were given the medicine including one portion of aspirin and five of ascorbic acid (corresponding to 500 mg/kg/day of aspirin, 2.5 g/kg/day of ascorbic acid) for 6 days, then feeding was stopped for 24 hours. The mice were then immersed to their necks in water at 23° C. for 24 hours, and their stomachs were removed for observation of the extent of ulcers.

Three control groups were as follows: Control group A was exposed to stress by being immersed in water after being given 600 mg/kg/day aspirin; control group B was exposed to stress by being immersed in water after being fed with normal food (no aspirin or ascorbic acid); control group C was not exposed to stress after being fed with normal food.

The extent of stomach ulcers was expressed in the numerical value (ulcer index) by observation under the microscope, and calculated statistically.

Ulcer Index:

The ulcer index was expressed by the longer side of the length of the ulcer. When it was longer than 1 mm, the index was the actual length, but when less than 1 mm, the index was assumed to be 0.3 mm. If multiple ulcers were observed in a stomach, the summary of indices of ulcers were assumed to be the individual ulcer index. The unit of the ulcer index was (mm).

The results were as follows:

In control group C, which had not been exposed to conditions to develop stomach ulcers, the ulcer index was $0.3 \pm 0.7$ (mean$\pm$S.D., mm), i.e., the ulcer was hardly observed. In control group B that was exposed to stress the ulcer index was $3.9 \pm 3.3$, i.e., the ulcer was observed. Moreover, in control group A that was given aspirin and exposed to stress, severe ulcer occurred, and its index was $13.9 \pm 10.9$.

On the other hand, in the test group that was given the medicine provided in this invention, the ulcer index was $7.0 \pm 6.8$, i.e. injury to the stomach was remarkably improved despite the stress and aspirin. The difference of ulcer indices between the test group and control group A was significant ($p < 0.05$).

Side effects were then investigated. All mice were operated on to remove, observe and weigh internal organs, such as hearts and livers. But as far as the three groups that were given stress; control groups A, B, and the test group, there was no differences observed. So side effects, such as toxicity, were not observed.

The ulcer index of each group is shown in Table 1.

Example 2

Demonstration of the effect in rats —Effect of the medicine provided in the invention against ulcers concurrently caused by administration of aspirin and exposure to stress caused by immersion in water Male and female Sprague-Dawley rats (18 to 19 weeks of age, primarily weighing 236 to 510 grams) were given the medicine including one portion of aspirin and two of ascorbic acid (corresponding to 500 mg/kg/day aspirin, 1.0 g/kg/day ascorbic acid) for 6 days, then feeding was stopped for 24 hours. Then they were immersed to their necks in water at 23° C. for 20 hours, and their stomachs were removed for observation of the extent of ulcers. Three control groups were as follows: Control group A was exposed to stress by being immersed in water after administration of 500 mg/kg/day aspirin; control group B was exposed to stress by being immersed in water after being fed with normal food (no aspirin or ascorbic acid); control group C was not exposed to stress after being fed with normal food.

The extent of the stomach ulcer was expressed in the numerical value (ulcer index) by observation under the microscope, and statistically calculated.

As a result, as shown in FIG. 1 (photograph), the remarkable effect of the medicine against stomach ulcer caused by aspirin was confirmed.

Comparison of the ulcer indices was as follows: In the test group that was given the medicine provided in this invention, the ulcer was remarkably reduced in both male ($32.5 \pm 18.2$) and female ($32.4 \pm 11.5$) rats, compared with the control group A that was given aspirin and exposed to stress (male $83.4 \pm 10.8$, female $75.5 \pm 24.8$, $p < 0.01$).

Moreover, in the test group the ulcer was noted less than in the control group B that was given only stress (male $46.5 \pm 19.7$, female $50.5 \pm 24.1$). The differences between the test group and control group A, and between the test group and control group B, was significant $p < 0.01$.

The side effects were examined, but the observation of the intestines and comparison of their weights showed no significant differences, as far as the three groups that were given stress.

The ulcer index of each group is shown in Table 2.

Example 3

Demonstration of the effect in rats—Portion of aspirin and ascorbic acid 14 female Sprague-Dawley rats (20 weeks of age, primarily weighing 400 to 420 g) were divided into three groups. They were given the medicine provided in this invention or aspirin only for 6 days, then feeding was stopped for 24 hours. Then they were immersed to their necks in water at 23° C. for 20 hours, and their stomachs were removed for observation of the extent of ulcer.

Three test groups were set as follows: Test group 1 was given medicine containing 0.1 portion of ascorbic acid to one portion aspirin (corresponding to 500 mg/kg/day aspirin, 50 mg/kg/day ascorbic acid); test group 2 was given medicine containing the same quantity of ascorbic acid and aspirin (corresponding to 500 mg/kg/day aspirin, 500 mg/kg/day ascorbic acid).

The control group was given 500 mg/kg/day aspirin only.

The extent of the stomach ulcer was compared by observation of internal wall tissue and mechanically measuring the area of ulcer.

As a result, as shown in Table 3, the area of ulcer in the test group 1 was $14.4 \pm 14.3$ mm$^2$ and that in the test group 2 was $49.0 \pm 20.8$ mm$^2$, while that in the control group was $106.0 \pm 31.5$ mm$^2$. The outbreak of ulcers was significantly surpressed in both test groups, compared with the control group ($p < 0.01$).

These results suggest that the medicine provided in the invention can prevent the outbreak of gastric injury when the medicine contains more than 0.1 portion ascorbic acid to 1 portion of aspirin.

Further variations and modifications of the invention will become apparent to those skilled in the art from the foregoing and are intended to be encompassed by the claims appended hereto.

Japanese Priority Application 335087/89, filed on Dec. 26, 1989, is relied on and incorporated by reference.

TABLE 1

| Group | Male | Female | Total |
| --- | --- | --- | --- |
| Test group | $5.2 \pm 2.6$ | $9.3 \pm 9.8$ | $7.0 \pm 6.8$ |
| Control A | $11.2 \pm 4.5$ | $16.5 \pm 15.2$ | $13.9 \pm 10.9$ |
| Control B | $5.3 \pm 1.5$ | $2.4 \pm 3.3$ | $3.9 \pm 3.3$ |
| Control C | $0.6 \pm 1.0$ | 0 | $0.3 \pm 0.7$ |

Ulcer Index: Mean ± S.D. (mm)
Number of test animals: 20 in each group
The value in the test group significantly differs from that in the control group A ($p < 0.05$).

TABLE 2

| Group | Male | Female | Total |
| --- | --- | --- | --- |
| Test group | $32.5 \pm 18.2$ | $32.4 \pm 11.5$ | $29.8 \pm 13.3$ |
| Control A | $83.4 \pm 10.8$ | $75.5 \pm 24.8$ | $78.1 \pm 20.8$ |
| Control B | $46.5 \pm 19.7$ | $50.5 \pm 24.1$ | $48.3 \pm 20.8$ |
| Control C | 0 | 0 | 0 |

Ulcer Index: Mean ± S.D. (mm)
Number of test animals: 20 in each group
The value in the test group significantly differs from that in the control groups A and B ($p < 0.01$).

TABLE 3

| Group | Number | Area of Ulcer |
| --- | --- | --- |
| Test group 1 | 5 | $14.4 \pm 14.3$ |
| Test group 2 | 5 | $49.0 \pm 20.8$ |
| Control group | 4 | $106.0 \pm 31.5$ |

Area of Ulcer: Mean ± S.D. (mm$^2$)
Both of the values in the test groups 1 and 2 significantly differ from that in the control group ($p < 0.01$).

What is claimed is:

1. A method for reducing the side effects of aspirin in a mammal, comprising administering to a mammal in need thereof an effective amount of a pharmaceutical composition comprising (a) at least one member selected from the group consisting of ascorbic acid and derivatives of ascorbic acid and (b) at least one member selected from the group consisting of aspirin and derivatives of aspirin.

2. The method according to claim 1, wherein said derivative of ascorbic acid is an inorganic salt of ascorbic acid.

3. The method according to claim 2, wherein said inorganic salt of ascorbic acid is sodium ascorbate.

4. The method according to claim 1, wherein said derivative of ascorbic acid is an ester of ascorbic acid and an inorganic acid.

5. The method according to claim 4, wherein said ester of ascorbic acid and an inorganic acid is phosphoric ascorbate.

6. The method according to claim 1, wherein said derivative of aspirin is selected from the group consisting of aluminum acetylsalicylate, cholin salicylate, and sodium salicylate.

7. The method according to claim 1, wherein the ratio of ascorbic acid and derivatives of ascorbic acid:aspirin and derivatives of aspirin is at least 1:10.

8. The method according to claim 1, wherein said pharmaceutical composition further comprises silica or starch or silica and starch.

9. The method according to claim 1, wherein said pharmaceutical composition further comprises acetaminophen.

10. The method according to claim 1, wherein said pharmaceutical composition optionally contains starch and is contained in a gelatin capsule.

11. The method according to claim 1, wherein said derivative of ascorbic acid is an ester of ascorbic acid.

12. The method according to claim 11, wherein said ester of ascorbic acid is mono stearyl ascorbate.

13. The method according to claim 1, wherein said pharmaceutical composition further comprises at least one pharmaceutically acceptable carrier.

14. The method according to claim 1, wherein said pharmaceutical composition further comprises at least one pharmaceutical excipient.

15. The method according to claim 1, wherein said component (a) is administered in a dosage from 50 mg to 2.5 g/kg/day.

* * * * *